Oct. 27, 1953 S. F. HAHN Plant Pat. 1,224
SANSEVIERIA PLANT
Filed Aug. 15, 1952
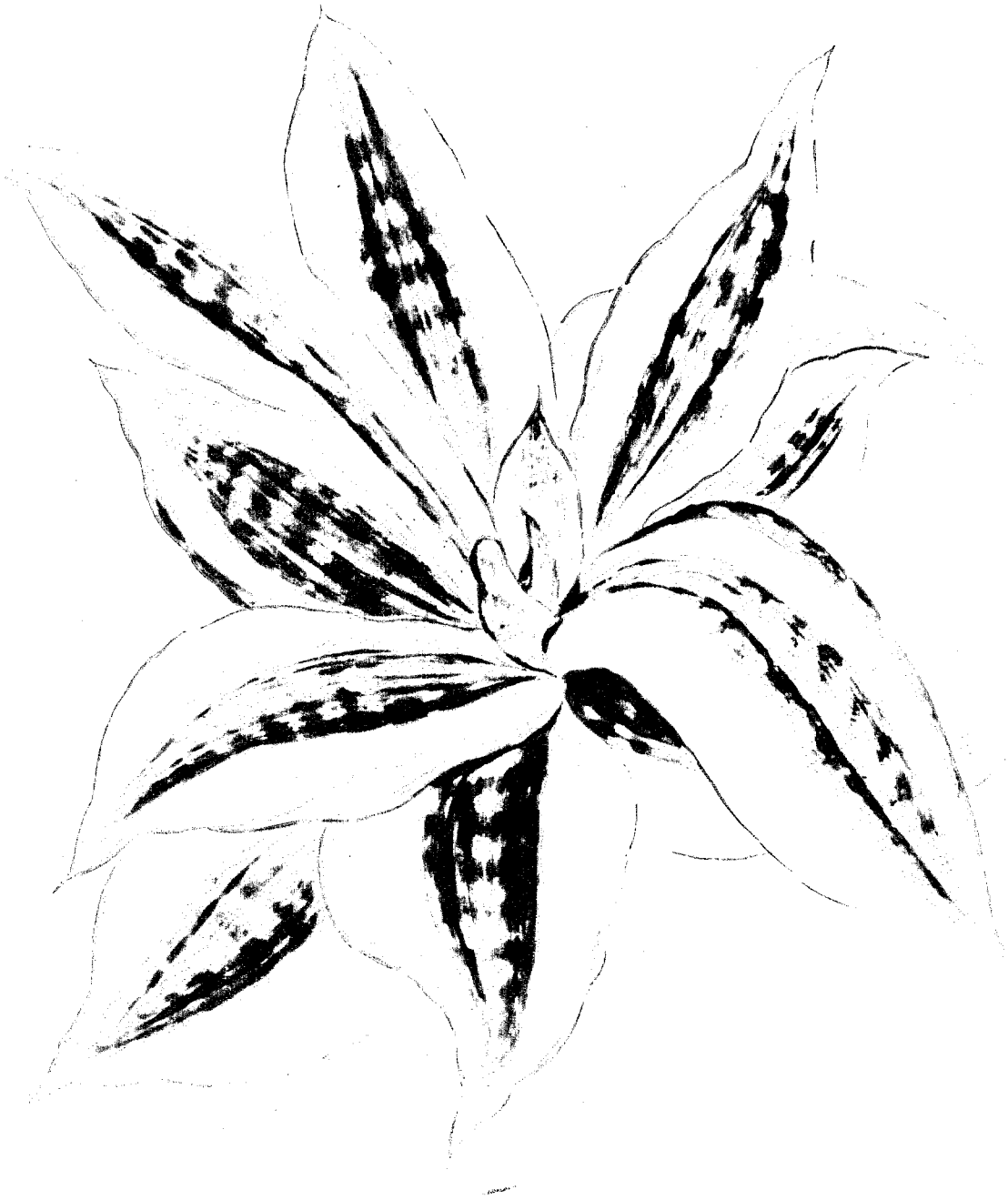
INVENTOR
Sylvan Frank Hahn
By Orville M. Kile
Plant Pat. Agent Patented Oct. 27, 1953

Plant Pat. 1,224

UNITED STATES PATENT OFFICE 1,224

SANSEVIERIA PLANT

Sylvan Frank Hahn, Pittsburgh, Pa.

Application August 15, 1952, Serial No. 304,663

1 Claim. (Cl. 47—59)

My present discovery pertains to a new variety of Sansevieria plant. This plant in its habit of spiral or rosette form of growth is identical to the subject of my United States Plant Patent No. 470, but the coloration of the foliage is so singularly different that it constitutes a readily distinguishable and useful new variety. Whereas the coloration and markings of the foliage in Plant Patent No. 470 are typically those of the *Sansevieria zeylonica*, my new variety posseses a golden yellow coloration in its foliage.

This new variety is a sport of Plant Patent No. 470, known in the trade as Sansevieria Hahnii. It was discovered by me in my greenhouses located in New Orleans, Louisiana.

This variety has been asexually reproduced by suckers (stoloniferous rhizomes which arise from adventitious buds), by me at my greenhouses above mentioned. It reproduces true to type from suckers but will not come true when propagated from leaf cuttings.

The illustration accompanying this application gives a view looking down into the plant from above. It shows the leaf arrangement and shape as well as the typical foliage coloration as nearly as the artist can portray them, in a plant when two years old. It must be understood, however, that there will be some variation between specimens. The relative widths of the yellow and the green bands will vary somewhat and the contrasts between these colors are more marked in some specimens.

Following is a detailed description of this new variety in which ordinary dictionary color terms are used except where color plates are cited, and such references are to Ridgway's Color Standards and Nomenclature.

Growth:

*Type.*—Compact, flat spiral or rosette; base of plant narrow and thin.

*Rapidity.*—Grows and reproduces rapidly and with ease. Reproduces true to type, however, only from suckers.

*Size.*—Original plant has attained a size of 18 inches in height after several years' growth.

Leaves:

*Shape.*—Much broader and shorter than other known varieties except the subject of Plant Patent No. 470 and sports therefrom. Narrow-ovate; very short point on older leaves. Young leaves concave; older leaves flat.

*Size.*—Average size 12 centimeters long by 6 centimeters broad through center.

*Margin.*—Entire; somewhat undulating.

*Color.*—From pale to golden yellow (approximately Barium Yellow to Strontian Yellow, Plate XVI), in longitudinal bands varying in width throughout the entire length of the leaf and alternate with bands of green color. In some plants the golden yellow bands occupy an area equal to two-thirds of the entire leaf area. The center or alternate bands are dark green in color (Spinach Green, Plate V), with transverse silver gray (Mineral Gray, Plate XLVII) colored bands. Nearer the edges some leaves have narrow light green bands (Dull Green-yellow, Plate XVII) running longitudinally.

*Position.*—Spreading from base; upper third horizontal to slightly reflexed.

*Base.*—Narrow.

Flowers: No flowers or fruit have ever been observed, although when the plants grow much older they may have such characters.

Having thus disclosed my discovery, I claim:

A new and distinct variety of Sansevieria plant of the spiral or rosette type, substantially as shown and described, characterized particularly by its bands of golden yellow color in the leaf and its habit of faithfully reproducing this color pattern only when propagated by using suckers.

SYLVAN FRANK HAHN.

No references cited.